United States Patent
Bastide et al.

(10) Patent No.: US 10,359,292 B2
(45) Date of Patent: Jul. 23, 2019

(54) DEEP LEARNING ALLERGEN MAPPING

(71) Applicant: International Business Machines Corporation, Armonk, NY (US)

(72) Inventors: Paul R. Bastide, Boxford, MA (US); Anca Sailer, Scarsdale, NY (US); Benjamin C. Wisnewski, Columbia, MO (US); Mattia Tomasoni, Dublin (IE); Sunil K. Mishra, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 15/479,720

(22) Filed: Apr. 5, 2017

(65) Prior Publication Data

US 2018/0292220 A1    Oct. 11, 2018

(51) Int. Cl.
| | | |
|---|---|---|
| G06N 20/00 | (2019.01) | |
| G06F 16/951 | (2019.01) | |
| G01C 21/34 | (2006.01) | |
| G01C 21/36 | (2006.01) | |
| G06F 16/29 | (2019.01) | |

(52) U.S. Cl.
CPC ..... *G01C 21/3415* (2013.01); *G01C 21/3461* (2013.01); *G01C 21/3691* (2013.01); *G06F 16/29* (2019.01); *G06F 16/951* (2019.01); *G06N 20/00* (2019.01)

(58) Field of Classification Search
CPC ............ G01C 21/3415; G01C 21/3461; G01C 21/3691; G06F 17/30864; G06N 99/005
See application file for complete search history.

(56) References Cited

U.S. PATENT DOCUMENTS

| | | | |
|---|---|---|---|
| 9,000,933 B2* | 4/2015 | Ray | G08B 21/043 340/627 |
| 9,053,483 B2 | 6/2015 | Geisner et al. | |
| 9,659,225 B2* | 5/2017 | Joshi | G06Q 50/12 |
| 2004/0166123 A1 | 8/2004 | Jacobi et al. | |
| 2012/0233033 A1 | 9/2012 | Calman et al. | |
| 2013/0048737 A1 | 2/2013 | Baym et al. | |
| 2013/0081053 A1 | 3/2013 | Levien et al. | |
| 2014/0058755 A1* | 2/2014 | Macoviak | G06F 19/328 705/3 |
| 2014/0201126 A1* | 7/2014 | Zadeh | G06K 9/627 706/52 |
| 2015/0100516 A1 | 4/2015 | Hicks et al. | |

(Continued)

OTHER PUBLICATIONS

Unknown, "Allergy Facts", American College of Allergy, Asthma & Immunology © 2014, printed on Feb. 22, 2017, 6 pages. http://acaai.org/news/facts-statistics/allergies.

(Continued)

*Primary Examiner* — Behrang Badii
*Assistant Examiner* — Daniel L Greene
(74) *Attorney, Agent, or Firm* — James L. Olsen (57) ABSTRACT

An entry on an allergen map may be generated by a computer system where a deep learning model is trained using online content data. Allergen content data which contains geographic data may be detected from the online content data. The allergen content data may be analyzed by the computer system and tagged with a quality and intensity indicator. Based on the tagging and the geographic location, an allergen map may be generated.

20 Claims, 5 Drawing Sheets

(56) References Cited

U.S. PATENT DOCUMENTS

| | | | |
|---|---|---|---|
| 2015/0242586 A1 | 8/2015 | Kagen | |
| 2015/0297776 A1* | 10/2015 | Conroy | G06Q 10/08 239/11 |
| 2016/0071432 A1 | 3/2016 | Kurowski et al. | |
| 2016/0202879 A1 | 7/2016 | Chen et al. | |
| 2016/0203352 A1 | 7/2016 | Marsico | |
| 2016/0224803 A1* | 8/2016 | Frank | G06F 21/6245 |
| 2016/0232625 A1 | 8/2016 | Akutagawa et al. | |
| 2016/0290912 A1 | 10/2016 | Kent et al. | |
| 2016/0300252 A1* | 10/2016 | Frank | G06Q 30/0203 |
| 2016/0328537 A1 | 11/2016 | Narula et al. | |
| 2016/0378950 A1 | 12/2016 | Reiner | |
| 2017/0108235 A1* | 4/2017 | Guan | F24F 11/0012 |
| 2017/0169017 A1* | 6/2017 | Byron | G06F 17/30684 |
| 2017/0281822 A1* | 10/2017 | Becker | A61L 9/015 |

OTHER PUBLICATIONS

Unknown, "The Economic Burden of Allergy", Prepared for World Allergy Week Apr. 4-10, 2011, World Allergy Organization, 1 page. http://www.worldallergy.org/UserFiles/file/Economic-Burden-of-Allergy.pdf.

Unknown, "Allergy Facts and Figures", AAFA.org, Asthma and Allergy Foundation of America, Copyright 1995-2017, 3 pages, printed on Feb. 22, 2017. http://www.aafa.org/page/allergy-facts.aspx.

Murphy, "Epinephrine Auto-Injector Protocol for Emergency Anaphylaxis in Schools", DNP Innovation Institute, Sep. 2012, 24 pages.

Unknown, "The Raft of Food Allergies: Inside the Allergic-Kid Economy", GOOD, Jul. 24, 2011, Copyright 2016 GOOD Worldwide Inc., 14 pages, printed on May 31, 2016.

Pistiner, "Superman, Food Allergy and Social Media", Blog @ AllergyHome.org, © 2011 AllergyHome.org LLC, 6 pages, printed on May 31, 2016. http://www.allergyhome.org/blogger/superman-food-allergy-and-social-media/.

Dimov et al., "Utilizing social networks, blogging and YouTube in allergy and immunology practices", Expert Review of clinical Immunology, published Jul. 10, 2015, 5 pages, http://dx.doi.org/10.1586/1744666X.2015.1065731.

Unknown, "Social Media Policy", Asthma & Allergy Center, Copyright 2013 Allergy & Immunology, PLC., 2 pages, printed on May 31, 2016. http://www.asthmaandallergycenter.net/legal/social-media.

National Allergy Map, Pollen.com, Copyright 2016 IMS Health Incorporated, Page last modified May 31, 2016, last printed on May 31, 2016, 2 pages. https://www.pollen.com/map.

Tree Pollen Map, weather.com, The Weather Channel, 1 page, printed May 31, 2016. https://weather.com/maps/health/allergies/treepollen.

Allergy Tracker for Boston, MA, weather.com, The Weather Channel, Copyright 1995-2016, The Weather Channel, LLC weather.com, 5 pages printed May 31, 2016. https://weather.com/forecast/allergy/l/USMA0046:1:US.

Seasonal Allergy Social Map, Copyright 2016 Healthgrades Operating Company, Inc., 2 pages, printed May 31, 2016. http://healthguides.healthgrades.com/finding-seasonal-allergy-relief/se...

Tanno et al., "Constructing a classification of hypersensitivity/allergic diseases for ICD-11 by crowdsourcing the allergist community", Allergy, European Journal of Allergy and Clinical Immunology, © 2015 John Wiley & Sons A/S. Published by John Wiley & Sons Ltd, 7 pages. http://onlinelibrary.wiley.com/doi/10.1111/all.12604/epdf.

Unknown, "Could I Be Allergic? Discover Your Allergy Triggers", MedicineNet.com, Reviewed Sep. 1, 2016, © 1996-2017 WebMD, LLC., 2 pages, printed Feb. 22, 2017. http://www.medicinenet.com/10_common_allergy_triggers_slideshow/article.htm.

Lee et al., "Mining social media streams to improve public health allergy surveillance", 2015 IEEE/ACM International Conference on Advances in Social Networks Analysis and Mining, ASONAM '15, Aug. 25-28, 2015, Copyright ACM, DOI: 10.1145/2808797.2808896, 8 pages.

Mell et al., "The NIST Definition of Cloud Computing", Recommendations of the National Institute of Standards and Technology, U.S. Department of Commerce, Sep. 2011, 7 pages.

"Accelerated Examination Support Document", International Business Machines Corporation, dated Sep. 12, 2017, 15 pages.

List of IBM Patents or Patent Applications Treated as Related, dated Sep. 12, 2017, pp. 1-2.

Bastide et al., "Deep Learning Allergen Mapping", U.S. Appl. No. 15/704,550, filed Sep. 14, 2017.

\* cited by examiner

DEEP LEARNING ALLERGEN MAPPING

BACKGROUND

The present disclosure relates to machine learning, and more specifically, to deep learning.

Deep learning, or deep structured learning, is a type of machine learning based on a set of algorithms that attempt to model high level abstractions in data. Some types of deep machine learning may be based loosely on information processing and communication patterns in the nervous system. Deep learning architecture include deep neural networks, convolution deep neural networks, deep belief networks, and recurrent neural networks may be applied to computer vision, automatic speech recognition, natural language processing, and bioinformatics.

SUMMARY

Embodiments of the present disclosure may be directed toward a method for generating an allergen map. The method may begin by providing, to a deep learning model, a set of online content data, wherein the deep learning model is trained using the online content data. Allergen content data that includes a geographic location may be detected from the set of online content data. The allergen content data may be analyzed and tagged. The tagging may include a quality indicator and an intensity indicator based on the analyzing. An entry on an allergen map may be generated based on the tagging and the geographic location.

Embodiments of the present disclosure may be directed toward a computer system comprised of at least one computer processor circuit configured to perform a method. The method may begin by providing, to a deep learning model, a set of online content data, wherein the deep learning model is trained using the online content data. Allergen content data that includes a geographic location may be detected from the set of online content data. The allergen content data may be analyzed and tagged. The tagging may include a quality indicator and an intensity indicator based on the analyzing. An entry on an allergen map may be generated based on the tagging and the geographic location.

Embodiments of the present disclosure may be directed toward a computer program product comprising a computer readable storage medium having program instructions embodied therewith, wherein the compute readable storage medium is not a transitory signal per se, the program instructions executable by a computer processing circuit to cause the circuit to perform a method. The method may begin by providing, to a deep learning model, a set of online content data, wherein the deep learning model is trained using the online content data. Allergen content data that includes a geographic location may be detected from the set of online content data. The allergen content data may be analyzed and tagged. The tagging may include a quality indicator and an intensity indicator based on the analyzing. An entry on an allergen map may be generated based on the tagging and the geographic location.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to machine learning, more particular aspects relate to deep learning. While the present disclosure is not necessarily limited to such applications, various aspects of the disclosure may be appreciated through a discussion of various examples using this context.

Immune systems may protect humans from invasive, illness-causing organisms (e.g., pathogens). In certain cases, an immune system may mistake an otherwise harmless substance for an invasive element. In this case, the substance may be called an allergen and the phenomena of the immune response may be knowns as an allergic reaction. Allergens are a very common chronic condition worldwide; while they remain underreported, they are increasingly impactful. Allergies can be dangerous to individuals and costly to society. For example, allergies may result in direct costs for medication and health care provision or tangential costs including loss of work or labor force, social support, loss of taxation income, home modifications, and lower productivity at work, to name a few.

Allergies may be caused by substances that are introduced to the body by ingestion or absorption through the skin. In some instances, these allergic reactions can be controlled by careful monitoring of food intake or contact with particular chemicals.

Further, some allergens may enter the body via the respiratory system. These allergens may be known as aeroallergens; exposure to aeroallergens may be very difficult to prevent. In some cases, aeroallergenic reactions may be prevented by gathering information regarding the level, distribution, localization, spreading, and rise of airborne allergens. The data may be distributed for use by those potentially impacted by aeroallergens, for example, it may be visually distributed using a heat map. A heat map or heatmap may be a map (e.g., a graphical representation) of data where individual data points or individual values may be represented by colors. An accurate geographical location and time relative to the collected data may be helpful in the utilization of the aeroallergenic information.

Figure 1:
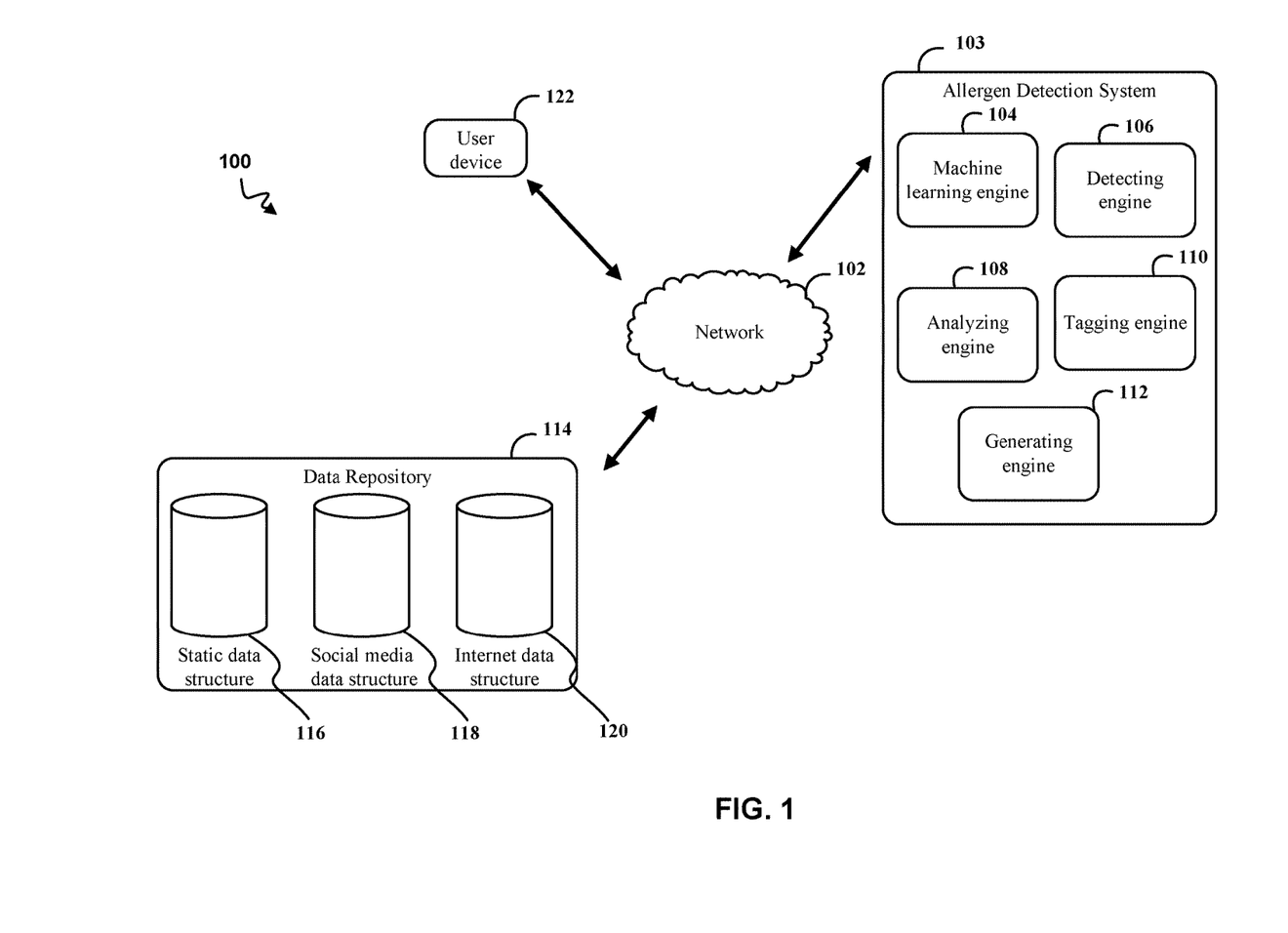
FIG. 1 depicts a diagram of a system for generating an allergen map based on machine learning detection of the allergens, according to embodiments.

FIG. 1 depicts a diagram of a system 100 for generating an allergen map based on machine learning detection of the allergens, consistent with embodiments. In embodiments, the system 100 may comprise an allergen detection system (ADS) 103 which may be a computer system or systems and may execute a series of commands over one or more processor circuits. The ADS 103 may have one or more engines, including the engines depicted here, more, or fewer engines. For example, the engines may include a machine learning engine 104, a detecting engine, 106, an analyzing engine 108, a tagging engine 110, and a generating engine 112. In embodiments, the machine learning engine may be a sub-engine of the detecting engine 106, the analyzing engine 108, and the tagging engine 110. Thus, the engine 106-110 may communicate with the machine learning engine 104 to make use of machine learning techniques.

The ADS 103 may send or receive data over one or more networks, including for example, network 102. The networks can include, but are not limited to, local area networks, point-to-point communications, wide area networks, the global Internet, and combinations thereof.

In embodiments, the detecting engine 106 of the ADS 103 may access data from one or more data structures in a data repository 114 over the network 102. The detecting engine 106 may provide this data to the machine learning engine 104, in order to train or improve the deep learning model of the machine learning engine 104. The deep learning model may be trained using a set of known online data, where this online data contains known allergen data. For example, the machine learning engine 104 may use supervised or semi-supervised learning techniques to learn about allergens by being fed online data that contains know allergen data (e.g., types of allergens, photos of allergens, videos of allergic reactions, or others), as described herein.

The detecting engine 106 may access data from a static data structure 116, which could include a set of data from resources including immunological response data sourced from, for example, medical textbooks, peer reviewed journal articles, encyclopedias or other sources. The static data structure 116 could also include allergen data including sources of allergens and data about the allergen sources from, for example, horticulture or botany texts, journal articles, encyclopedias, or other data. The static data structure 116 could also include geographic data, weather pattern data, seasonal data, or other data sourced from maps, geography textbooks, or other data sources. The data in this structure 116 could be updated once, at regular intervals, as needed, or in another way. The detecting engine 106 could provide this data to the machine learning engine 104, as discussed above.

The detecting engine 106 may also access data from a social media data structure 118 and an internet data structure 120. The detecting engine 106 may access or receive data from other or fewer sources than those mentioned for its training. The social media data structure 118 may contain data sourced from social media profiles across the Internet. In embodiments, the types of social media sources may be selected or limited (e.g., a particular account or set of accounts may be used, a particular geographic location may be selected, or the data may be filtered in some other way). In embodiments, the social media data structure 118 may be updated iteratively, based on a user setting or responsive to new published content. For example, the social media data structure 118 could update upon detecting a new post on a social media site.

The detecting engine 106 may also access data from an internet data structure 120. In embodiments, the internet data structure 120 could contain data from Internet webpages, blog posts, university sites, or other Internet-based sources. This data could be relevant to allergen sources, allergen resources, immunological responses, or other data deemed useful in training the machine learning engine 104 of the ADS 103. For example, the data could contain allergic reaction indicators such as a sneeze, dark undereye circles indicative of allergies, conjunctivitis, comments, or other indicators.

In embodiments, the detecting engine 106 and analyzing engine 108 may be integrated with the machine learning engine 104 or they may be separate entities in communication with the machine learning engine 104. For ease of discussion, they will be referred to individually throughout the figure discussion. In embodiments, the detecting engine 106 may detect allergen content data from a data source, for example, the social media data structure 118. This allergen content data may be associated with a particular geographic location, for example, it may have been posted from a smart phone with an enabled global positioning service (GPS) feature. For example, the detecting engine 106 may detect that a new post has been shared via a smartphone located in San Diego, Calif. The detecting engine 106, as informed by the machine learning engine 104, may detect that this post is a video of an allergic reaction taking place (e.g., a sneezing or coughing human). The engine may then pass the data to the analyzing engine 108, for analysis based on the ability of the machine learning engine 104 to recognize an allergic reaction. For example, the analyzing engine 108 could determine that the post (e.g., the video of the sneezing), was very likely allergen content data, and related to an allergic reaction, rather than, for example, a cold or simply dust in the air.

In embodiments, the data could then be passed to the tagging engine 110, and the tagging engine could tag, based on the analyzing, the allergen content data. The tagging engine 110 could tag the data with both a quality indicator and an intensity indicator. In communication with the machine learning engine 104, the tagging engine 110 may tag the allergen data with an intensity indicator, indicating the level of intensity at which the allergen may be impactful. For example, an intensity indicator tag could indicate that a particularly allergen-producing flower is in full bloom (versus, for example, an end of the season bloom), indicating a high level of allergen activity for the particular flower photographed or described in the tagged piece of allergen content data. The tagging engine 110 may also tag the allergen data with a quality indicator. The quality indicator could indicate what kind or type of allergen is identified within the allergen data. For example, a photo of a particular type of flower that was determined to be an allergen-producer may receive a quality tag which indicates the type of pollen produced by the flower. The quality tag could also indicate that the allergen was plant based, or seasonal, an aeroallergen, or it may be tagged in another way to indicate a relevant type.

In embodiments, the tagging engine 110 of the ADS 103 may then pass the tagged data to the generating engine 112. The generating engine 112 may use the tag or tags as well as the geographical information associated with the allergen data to generate an entry for an allergen heat map. The entry may appear at a particular location on the map with one or more text, image, video, or other data messages, indicating various aspects of the allergen data. This entry may aggregate with other entries to create an allergen heat map, which may present the strength of various allergens within a particular area. The map may be communicated to or accessed by one or more remote devices or systems, for example user device 122, over the network 102.

In embodiments, the map generated by the allergen entries may be updated, modified, filtered, and/or personalized in a variety of ways. For example, the map may be personalized for a particular user or demographic of users' individual allergies. The map may be filtered to show historical allergen data, for example, over a particular season, or at a particular altitude. In this way, the map could be used by a user planning his or her travel, in order to anticipate impending allergic reactions. For example, the data in a heat map could also be used by the system to generate a new or alternate travel route for a user. The data could also be communicated across the system or to another system to a maps or travel route planning application. The application may use the data to generate an allergen-informed travel route. In embodiments, the system generating engine 112 could also generate recommendations to a user to set of users to allow them to avoid the allergen or allergens. For example, the system could, responsive to a user's settings or profile (e.g., location, specific allergen sensitivities, or other characteristics), generate a recommendation such as "stay indoors," "avoid wooded areas," "travel between the hours of 7-9" or other recommendations relevant to the allergen map.

The map may also be used to predict future allergens. The map may be updated as new information is available, for example, based on new social media posts, new data regarding allergen pathology, updated weather forecasts, or other data.

Figure 2:
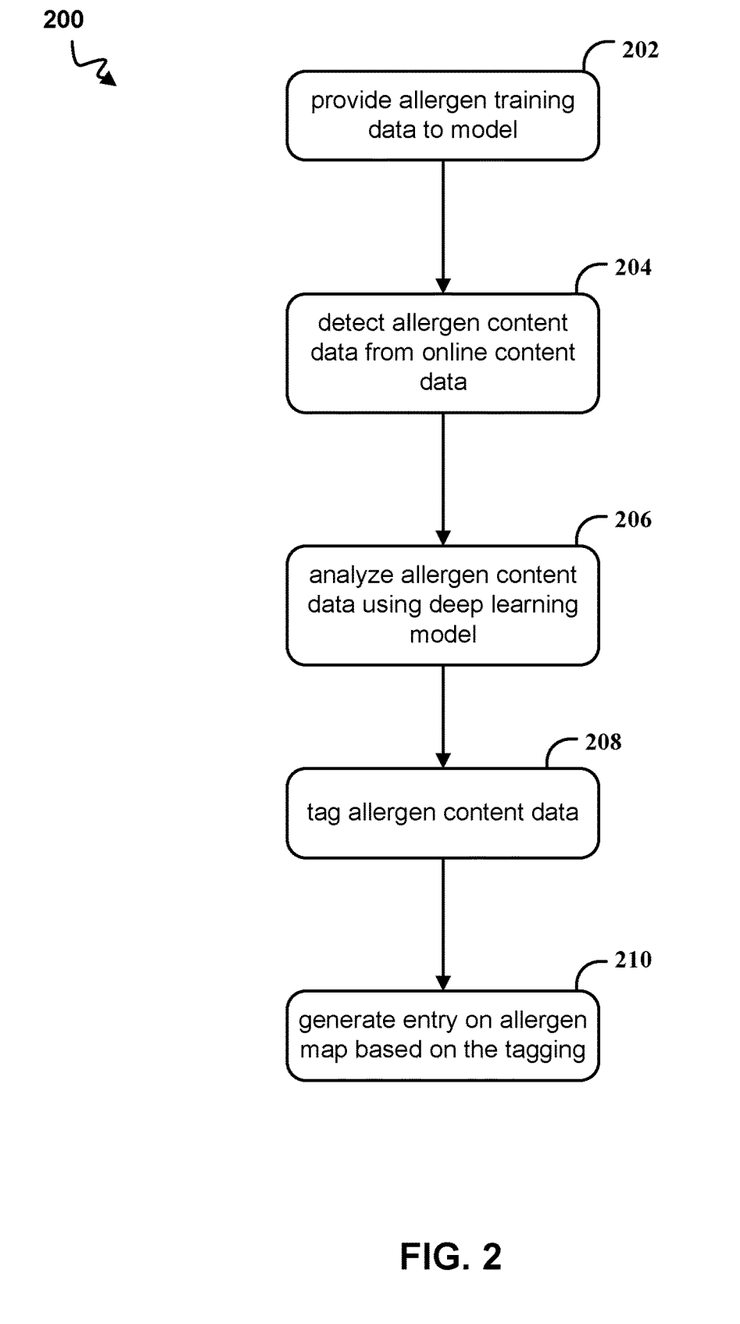
FIG. 2 depicts a flow of a method for generating an allergen map based on data obtained from the Internet, according to embodiments.

FIG. 2 depicts an example method 200 for generating an allergen map based on data obtained from the Internet, according to embodiments. The method 200 may begin by training a machine learning model using online content data, per 202. A set of online content data may be provided to the machine learning model. In embodiments, this may be a type of machine learning or artificial intelligence engine.

An AI engine can be configured to identify features of different allergens according to each allergen's characteristics. The engine may be configured to learn through the acquisition of training data, which can include the use of supervised, unsupervised or hybrid learning techniques. For example, predictive models can be used and may include appropriate supervised learning algorithms, such as regression models, artificial neural networks, support vector machines, and statistical classifiers, trained on data from the knowledge base, which can include objects presented to the classifier whose classes are known. This enables the classifier to then identify the characteristics, models and clusters according to class (e.g., by finding the cluster which most closely corresponds to the features extracted from the object). These features can then be used and applied to data sourced from social media or elsewhere online to identify the presence of an allergic reaction.

The data provided to the machine learning model, per 202, may be similar to the data contained in the data repository 114 of FIG. 1. In embodiments, the system, for example, an allergen detection system (ADS) like the one depicted at 103 of FIG. 1, may then detect allergen content data from incoming online content data, per 204. For example, a detecting engine (e.g., detecting engine 106 of FIG. 1) may detect allergen data in a newly posted social media post.

In embodiments, the detecting may include object recognition, including pictures and video. For example, the system could learn to detect various allergen-sources, such as trees, grasses, weeds, or flowers, and differentiate between them. In embodiments, this detection could occur in a photo or video of the plant itself, or the system could detect the particular vegetation from the background of a photo or video. Thus, content not specifically related to allergens or allergies could be detected as allergen content data and used to inform and/or improve the allergen map. The system could also learn to detect animals, such as cats, dogs, or bees, which may cause an allergic reaction.

In embodiments, the system could also learn to detect various foodstuffs or edibles from photos, videos, audio, or text, which could be potential allergens. For example, the system could identify peanuts in a photo of a dish at a restaurant or from a posted menu. The system could also indicate that this is a potential allergen.

The system may then analyze the allergen content data, per 206, in communication with the deep learning model, and tag the data, as described in FIG. 1. As part of the analyzing, the system could analyze the allergen data for characteristics including quality and intensity. Based on the analyzing, the system could then tag the data, per 208. In embodiments, this tagging could be performed by an engine, for example tagging engine 110 of FIG. 1, and could include tagging with a quality indicator as well as an intensity indicator. As discussed herein, the quality indicator could identify the type of allergen (e.g., pollen, dust, or food-borne) and the intensity indicator could identify the level or severity of the allergen. These tags could later be used in map generation, as discussed at step 210. The detecting, analyzing, tagging steps may occur as part of the processing and generating of the map, as well as serve a training function in improving allergen recognition in the system.

In embodiments, the system may then generate an entry on an allergen map based on the tagging, per 210. For example, a flag, mark, or other indicator may be added to a map. An aggregate of these entries may then result in a heat map or other type of map which can convey, using colors or textures, visual data. For example, a particular color could indicate a higher concentration of a particular type of allergen in an area, with a different color indicating a lower concentration. In embodiments, color could be used to indicate the presence of a particular type of allergen. In embodiments, the generated maps could be sorted or filtered using the various tags attached at step 208. For example, a map could be sorted by intensity by a user or administrator. For example, entries on a heat map could be filtered to display only those entries with an intensity tag above a certain point, in a certain range, or in another way. As another example, entries on a heat map could be filtered based on the quality indicator. For example, a map could be generated wherein only the entries with a pollen tag are displayed. The map could be filtered using a combination of tags, as well. For example, a map could be generated based on a quality indicator (e.g., only tree sap allergens) and an intensity indicator (e.g., only above a particular level). The entries on the map could be filtered similarly for other characteristics not described, too, in order to generate a personalized map for a user or set of users.

Figure 3:
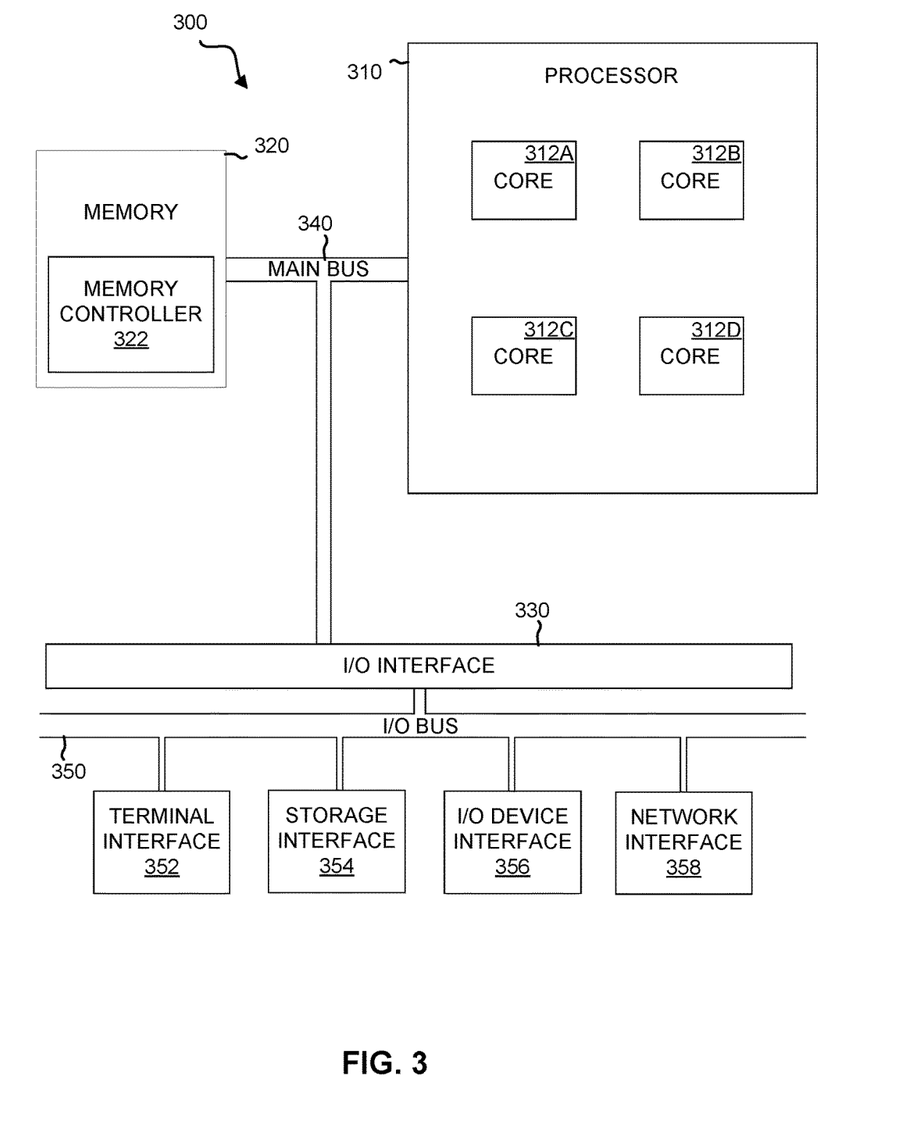
FIG. 3 depicts the representative major components of an example computer system 300 that may be used, according to embodiments.

FIG. 3 depicts the representative major components of an example computer system 300 that may be used, in accordance with embodiments of the present disclosure. It is appreciated that individual components may vary in complexity, number, type, and\or configuration. The particular examples disclosed are for example purposes only and are not necessarily the only such variations. The computer system 300 may comprise a processor 310, memory 320, an input/output interface (herein I/O or I/O interface) 330, and a main bus 340. The main bus 340 may provide communication pathways for the other components of the computer system 300. In some embodiments, the main bus 340 may connect to other components such as a specialized digital signal processor (not depicted).

The processor 310 of the computer system 300 may be comprised of one or more cores 312A, 312B, 312C, 312D (collectively 312). The processor 310 may additionally include one or more memory buffers or caches (not depicted) that provide temporary storage of instructions and data for the cores 312. The cores 312 may perform instructions on input provided from the caches or from the memory 320 and output the result to caches or the memory. The cores 312 may be comprised of one or more circuits configured to perform one or more methods consistent with embodiments of the present disclosure. In some embodiments, the computer system 300 may contain multiple processors 310. In some embodiments, the computer system 300 may be a single processor 310 with a singular core 312.

The memory 320 of the computer system 301 may include a memory controller 322. In some embodiments, the memory 320 may comprise a random-access semiconductor memory, storage device, or storage medium (either volatile or non-volatile) for storing data and programs. In some embodiments, the memory may be in the form of modules (e.g., dual in-line memory modules). The memory controller 322 may communicate with the processor 310, facilitating storage and retrieval of information in the memory 320. The memory controller 322 may communicate with the I/O interface 330, facilitating storage and retrieval of input or output in the memory 320.

The I/O interface 330 may comprise an I/O bus 350, a terminal interface 352, a storage interface 354, an I/O device interface 356, and a network interface 358. The I/O interface 330 may connect the main bus 340 to the I/O bus 350. The I/O interface 330 may direct instructions and data from the processor 310 and memory 320 to the various interfaces of the I/O bus 350. The I/O interface 330 may also direct instructions and data from the various interfaces of the I/O bus 350 to the processor 310 and memory 320. The various interfaces may include the terminal interface 352, the storage interface 354, the I/O device interface 356, and the network interface 358. In some embodiments, the various interfaces may include a subset of the aforementioned interfaces (e.g., an embedded computer system in an industrial application may not include the terminal interface 352 and the storage interface 354).

Logic modules throughout the computer system 300—including but not limited to the memory 320, the processor 310, and the I/O interface 330—may communicate failures and changes to one or more components to a hypervisor or operating system (not depicted). The hypervisor or the operating system may allocate the various resources available in the computer system 300 and track the location of data in memory 320 and of processes assigned to various cores 312. In embodiments that combine or rearrange elements, aspects and capabilities of the logic modules may be combined or redistributed. These variations would be apparent to one skilled in the art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
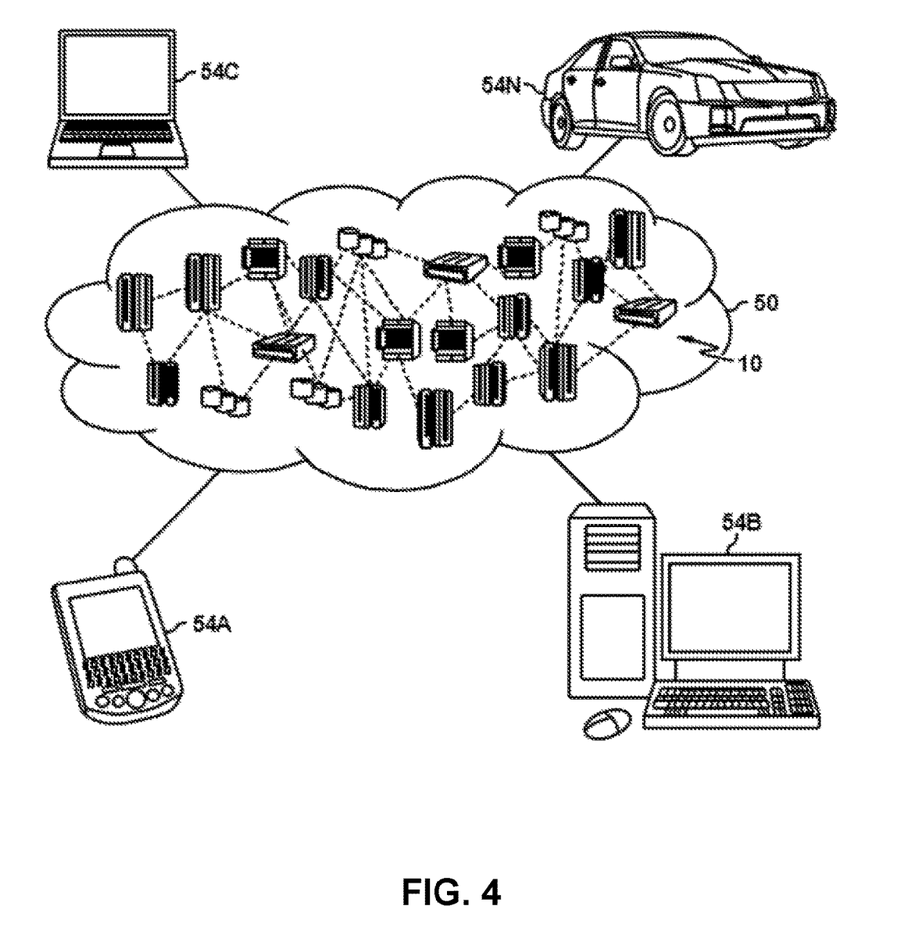
FIG. 4 depicts a cloud computing environment, according to embodiments.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
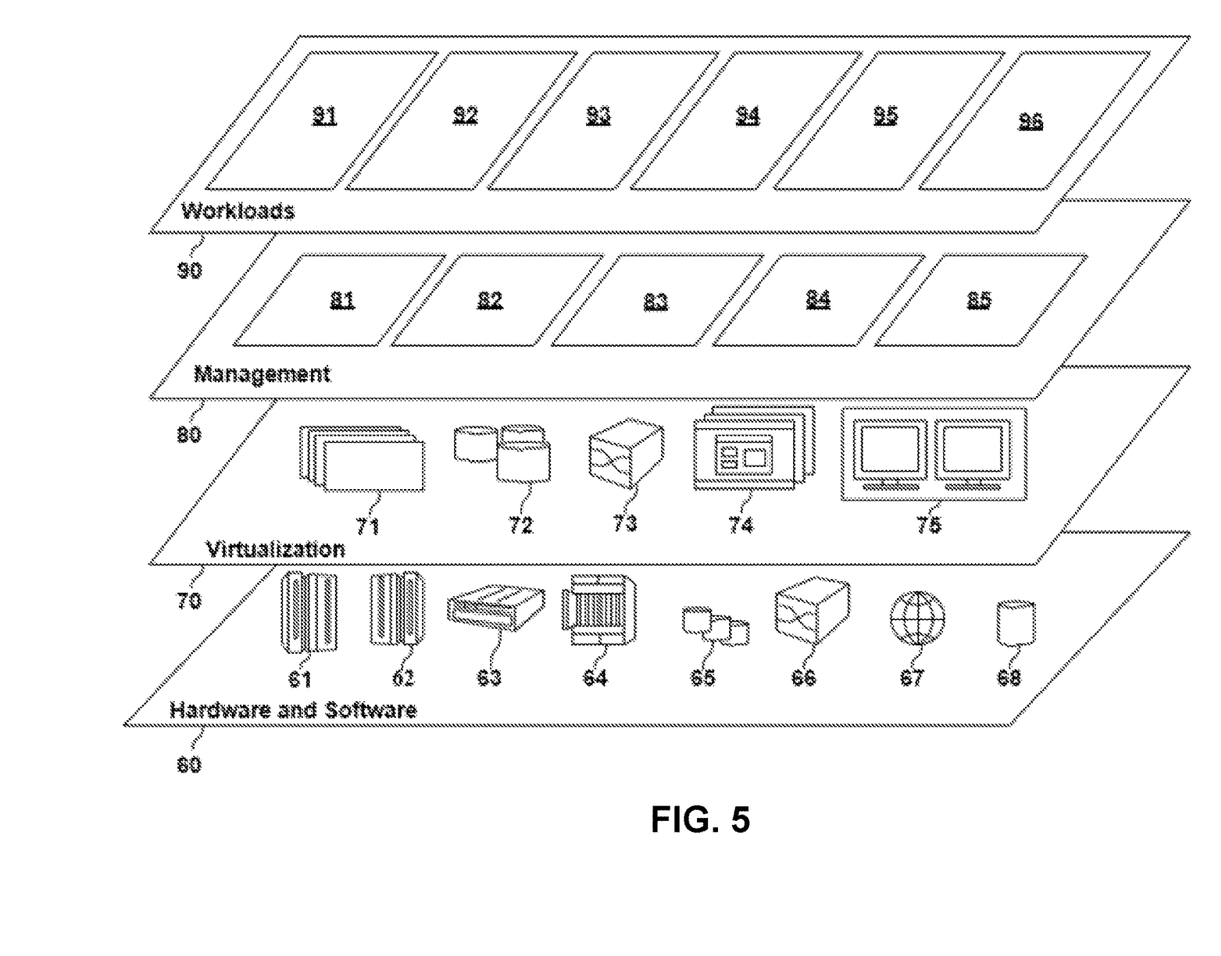
FIG. 5 depicts abstraction model layers, according to embodiments.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and allergen mapping 96.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method comprising:

providing, from a shared pool of configurable computing resources, to at least one computer processor circuit executing an artificial neural network, a set of known online content data, wherein the artificial neural network is trained using the known online content data, and wherein the known online content data comprises a set of known allergen data;

detecting, by the at least one computer processor circuit executing the artificial neural network, from a set of incoming online content data, allergen content data, wherein the allergen content data comprises a geographic location of a smart phone with an enabled global positioning service (GPS) feature, wherein the allergen content data includes a photograph taken by the smart phone, wherein the photograph includes a flower in a background of the photograph and detected by the artificial neural network using object recognition;

analyzing, by the at least one computer processor circuit executing the artificial neural network, the allergen content data;

tagging, by the at least one computer processor circuit executing the artificial neural network and based on the analyzing, the allergen content data, wherein the tagging comprises a quality indicator and an intensity indicator, wherein the quality indicator comprises a pollen associated with the flower in the background of the photograph, wherein the intensity indicator is based on a blooming season of the flower in the background of the photograph;

generating, by the at least one computer processor circuit executing the artificial neural network and based on the tagging and the geographic location, an entry on an allergen map;

filtering, by the at least one computer processor circuit executing the artificial neural network, the allergen map based on a profile of a user to show allergen entries having a first quality indicator and a first intensity indicator, wherein the profile of the user comprises a location of the user and allergen sensitivities of the user, the allergen sensitivities including the first quality indicator and the first intensity indicator;

displaying, by the at least one computer processor circuit executing the artificial neural network, the filtered allergen map on a device of the user; and providing, by the at least one computer processor circuit executing the artificial neural network, a recommendation to the device based on the filtered allergen map.

2. The method of claim 1, wherein the providing comprises applying, to the allergen content data, object recognition and natural language processing.

3. The method of claim 1, wherein the online content data is collected via data mining across the Internet.

4. The method of claim 1, wherein the online content data comprises photographic content and video content, wherein the photographic content comprises photographs of allergens selected from a group consisting of: plants, animals, and foods, wherein the video content comprises videos of allergic reactions.

5. The method of claim 1, wherein the quality indicator conveys an allergen detected in the allergen content data, wherein the allergen is selected from a group consisting of: a pollen allergen, a dust allergen, and a food-borne allergen.

6. The method of claim 1, wherein the intensity indicator conveys a particular level of intensity of an allergen detected in the allergen content data.

7. The method of claim 1, further comprising:
generating, in response to the generating the entry on the allergen map, a set of new allergen entries on the allergen map;
generating, based on the allergen map and a profile of a user, an alternate travel route for the user, wherein the profile of the user comprises a location of the user and allergen sensitivities of the user; and
generating, based on the allergen map and the profile of the user, a recommendation to the user.

8. The method of claim 1, wherein the entry on the allergen map comprises a flag on the allergen map.

9. A computer system comprising at least one computer processor circuit configured to perform a method comprising:
providing, from a shared pool of configurable computing resources, to the at least one computer processor circuit executing an artificial neural network, a set of known online content data, wherein the artificial neural network is trained using the known online content data, and wherein the known online content data comprises a set of known allergen data;
detecting, by the at least one computer processor circuit executing the artificial neural network and from a set of incoming online content data, allergen content data, wherein the allergen content data comprises a geographic location of a smart phone with an enabled global positioning service (GPS) feature, wherein the allergen content data includes a photograph taken by the smart phone, wherein the photograph includes a flower in a background of the photograph and detected by the artificial neural network using object recognition;

analyzing, by the at least one computer processor circuit executing the artificial neural network, the allergen content data;

tagging, by the at least one computer processor circuit executing the artificial neural network and based on the analyzing, the allergen content data, wherein the tagging comprises a quality indicator and an intensity indicator, wherein the quality indicator comprises a pollen associated with the flower in the background of the photograph, wherein the intensity indicator is based on a blooming season of the flower in the background of the photograph;

generating, by the at least one computer processor executing the artificial neural network and based on the tagging and the geographic location, an entry on an allergen map filtering, by the at least one computer processor circuit executing the artificial neural network, the allergen map based on a profile of a user to show allergen entries having a first quality indicator and a first intensity indicator, wherein the profile of the user comprises a location of the user and allergen sensitivities of the user, the allergen sensitivities including the first quality indicator and the first intensity indicator;

displaying, by the at least one computer processor circuit executing the artificial neural network, the filtered allergen map on a device of the user; and providing, by the at least one computer processor circuit executing the artificial neural network, a recommendation to the device based on the filtered allergen map.

10. The computer system of claim 9, wherein the providing comprises applying, to the allergen content data, object recognition and natural language processing.

11. The computer system of claim 9, wherein the online content data is collected via data mining across the Internet.

12. The computer system of claim 9, wherein the online content data comprises photographic content and video content, wherein the photographic content comprises photographs of allergens selected from a group consisting of: plants, animals, and foods, wherein the video content comprises videos of allergic reactions.

13. The computer system of claim 9, wherein the quality indicator conveys an allergen detected in the allergen content data, wherein the allergen is selected from a group consisting of: a pollen allergen, a dust allergen, and a food-borne allergen.

14. The computer system of claim 9, wherein the intensity indicator conveys a particular level of intensity of an allergen detected in the allergen content data.

15. The computer system of claim 9, wherein the method further comprises:
generating, in response to the generating the entry on the allergen map, a set of new allergen entries on the allergen map;
generating, based on the allergen map and a profile of a user, an alternate travel route for the user, wherein the profile of the user comprises a location of the user and allergen sensitivities of the user; and
generating, based on the allergen map and the profile of the user, a recommendation to the user.

16. A computer program product comprising a computer readable storage medium having program instructions embodied therewith, wherein the computer readable storage medium is not a transitory signal per se, the program instructions executable by a computer processing circuit to cause the circuit to perform the method comprising:

providing, from a shared pool of configurable computing resources, to the computer processing circuit executing an artificial neural network, a set of known online content data, wherein the artificial neural network is trained using the known online content data, and wherein the known online content data comprises a set of known allergen data;

detecting, by the computer processing circuit executing the artificial neural network and from a set of incoming online content data, allergen content data, wherein the allergen content data comprises a geographic location of a smart phone with an enabled global positioning service (GPS) feature, wherein the allergen content data includes a photograph taken by the smart phone, wherein the photograph includes a flower in a background of the photograph and detected by the artificial neural network using object recognition;

analyzing, by the computer processing circuit executing the artificial neural network, the allergen content data;

tagging, by the computer processing circuit executing the artificial neural network and based on the analyzing, the allergen content data, wherein the tagging comprises a quality indicator and an intensity indicator, wherein the quality indicator comprises a pollen associated with the flower in the background of the photograph, wherein the intensity indicator is based on a blooming season of the flower in the background of the photograph;

generating, by the computer processing circuit executing the artificial neural network and based on the tagging and the geographic location, an entry on an allergen map filtering, by the at least one computer processor circuit executing the artificial neural network, the allergen map based on a profile of a user to show allergen entries having a first quality indicator and a first intensity indicator, wherein the profile of the user comprises a location of the user and allergen sensitivities of the user, the allergen sensitivities including the first quality indicator and the first intensity indicator;

displaying, by the at least one computer processor circuit executing the artificial neural network, the filtered allergen map on a device of the user; and providing, by the at least one computer processor circuit executing the artificial neural network, a recommendation to the device based on the filtered allergen map.

17. The computer program product of claim 16, wherein the providing comprises applying, to the allergen content data, object recognition and natural language processing.

18. The computer program product of claim 16, wherein the online content data comprises photographic content and video content, wherein the photographic content comprises photographs of allergens selected from a group consisting of: plants, animals, and foods, wherein the video content comprises videos of allergic reactions.

19. The computer program product of claim 16, wherein the quality indicator conveys an allergen detected in the allergen content data, wherein the allergen is selected from a group consisting of: a pollen allergen, a dust allergen, and a food-borne allergen.

20. The computer program product of claim 16, wherein the method further comprises:

generating, in response to the generating the entry on the allergen map, a set of new allergen entries on the allergen map;

generating, based on the allergen map and a profile of a user, an alternate travel route for the user, wherein the profile of the user comprises a location of the user and allergen sensitivities of the user; and generating, based on the allergen map and the profile of the user, a recommendation to the user.

\* \* \* \* \*